United States Patent [19]
La Balme

[11] 3,946,724
[45] Mar. 30, 1976

[54] DEVICE FOR MEASURING PRESSURE

[75] Inventor: Maurice La Balme, Saint Cloud, France

[73] Assignee: Thomson Medical-Telco, Paris, France

[22] Filed: Apr. 1, 1974

[21] Appl. No.: 456,475

[30] Foreign Application Priority Data
Apr. 9, 1973  France .................. 73.12666

[52] U.S. Cl. ....... 128/2.05 E; 73/398 R; 128/2.05 D
[51] Int. Cl.² .................................. A61B 5/02
[58] Field of Search ..... 128/2.05 D, 2.05 E, 2.05 T, 128/2.05 P, 2.06 E, 2.06 F, DIG. 4; 73/398 AR, 398 R

[56] References Cited
UNITED STATES PATENTS

| | | | |
|---|---|---|---|
| 2,420,148 | 5/1947 | Ostergren | 73/398 AR |
| 3,088,323 | 5/1963 | Welkowitz et al. | 128/2.05 D |
| 3,138,027 | 6/1964 | Li | 73/398 AR |
| 3,341,794 | 9/1967 | Stedman | 73/398 AR X |
| 3,553,625 | 1/1971 | Stedman | 128/2.05 D |
| 3,572,322 | 3/1971 | Wade | 128/DIG. 4 X |
| 3,703,099 | 11/1972 | Rouse | 73/398 AR |
| 3,710,781 | 1/1973 | Hutchins et al. | 73/398 AR |
| 3,724,274 | 4/1973 | Millar | 73/398 AR |
| 3,818,765 | 6/1974 | Eriksen | 128/2.05 E |
| 3,831,588 | 8/1974 | Rindner | 128/2.05 E |

Primary Examiner—Kyle L. Howell
Attorney, Agent, or Firm—Roland Plottel

[57] ABSTRACT

A device which will find particular use as a medical catheter for measuring the pressure and rate at which blood flows through the heart and the blood vessels.

An integrated circuit chip having at least one field effect transistor thereon, which is sensitive to deformation of the chip is mounted at one end inside the device. An elastic membrane typically made from natural rubber, is mounted in an opening in the side of the device. An unattached core or plunger is positioned between the membrane and the other end of the semiconductor chip, thus when pressure is applied to the membrane, it deforms the chip and provides an electric signal.

6 Claims, 5 Drawing Figures

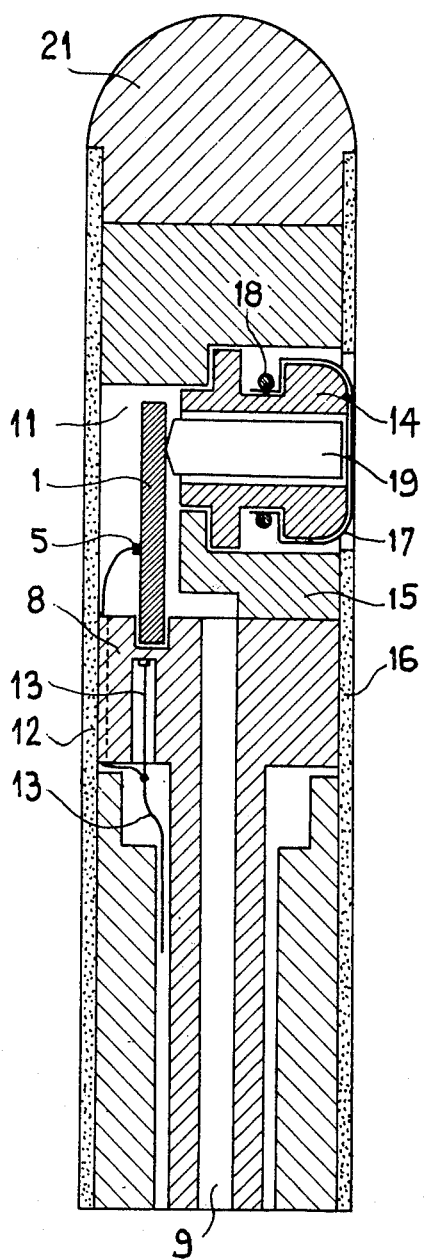
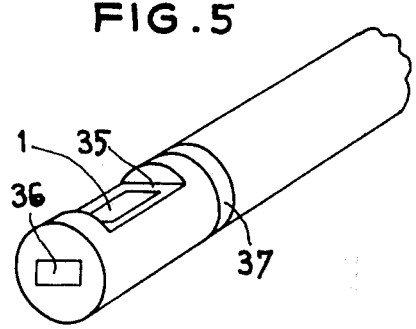
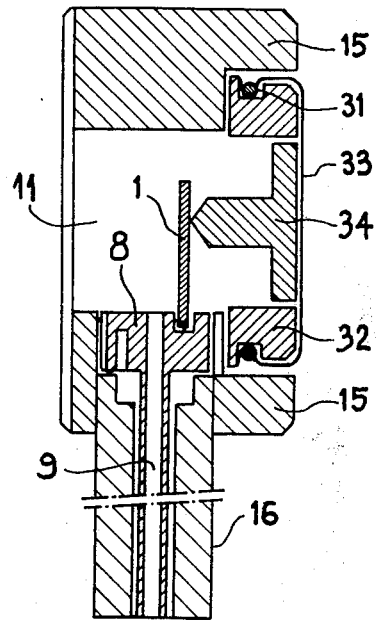

DEVICE FOR MEASURING PRESSURE

The invention relates to devices for measuring pressure and will find particular application for such measurements inside the heart or blood vessels.

Most systems found among the various devices currently available for measuring pressure are based on inductance variation created by displacement of a magnetic core in a solenoid to which pressure is applied. Other systems use strain gauges made by depositions on metal film or diffusions in silicon. These systems present certain disadvantages: —extremely low sensitivity and significant fluctuations from temperature due to the extremely small dimensions of the gauges. For example, strain gauges composed of Wheatstone bridges, powered by a voltage of about ten volts, deliver a signal varying from 5 to 50 mV depending on the technique used, for a pressure maximum of 300 mm Hg.

The strain gauge or transducer used in the present invention has an arrangement of field effect transistors in an integrated circuit formed in a silicon chip. This arrangement, known in the art, delivers a voltage in proportion to its elongation (deformation) with a sensitivity far greater than that of conventional resistive gauges.

The characteristics of this circuit are:

| | |
|---|---|
| Applied voltage | + 20 V |
| Power consumed | 20 m W |
| Output impedance | 100 K Ω |
| Gauge voltage factor | 1,000 |

The chip is subjected to deformation in proportion to the amount of pressure to be measured.

An object of this invention is to provide a measuring device with improved sensitivity.

According to one aspect of the invention, the chip subjected to displacement is composed of a substrate having the integrated circuit.

The thickness of the substrate has been reduced as well as its length in order to improve the sensitivity of the instrument and to increase the displacements of the substrate in relation to the strains to which it is subjected.

According to another aspect of the invention, that area of the substrate which constitutes the chip subjected to deformation consists of the integrated circuit with only the addition of a small portion needed to separate the substrates from one another during their manufacture.

In one embodiment, the device for measuring pressure includes a measuring chamber which contains a chip sensitive to deformations. The chip is mounted at one end in a fixed support (cantilevered), while at its other end it is subject to deformations provoked by pressure from the outside.

In the case of devices for measuring pressure, the unattached end of the chip responds to pressure outside the chamber transmitted to it by means of an impermeable elastic membrane which acts upon a core sliding within a mandrel. This core is itself in contact with the unattached end of the chip.

In order to improve the sensitivity of the pressure-measuring device, the membrane is made of a substance the elasticity of which remains constant in every direction in spite of temperature, and over a period of time.

In order to further increase sensitivity, pressure is transmitted by the elastic membrane to the chip through a core sliding freely within a support, this core being in contact with both membrane and chip without adhering in any way to either one.

In another embodiment, the device for measuring pressure consists of a measuring chamber with a flat surface into which a window has been cut.

According to the invention, the edges of the chip are fixed directly to the edges of the window.

Other characteristics of the invention will become apparent in the course of describing the various embodiments listed below:

FIG. 3 is a longitudinal cross-section view of a device for measuring pressure according to the invention mounted in a catheter.

FIG. 4 is a cross-section view of another embodiment of the device for measuring pressure.

FIG. 5 is a perspective view of a catheter having two pressure-measuring devices.

Figure 1:
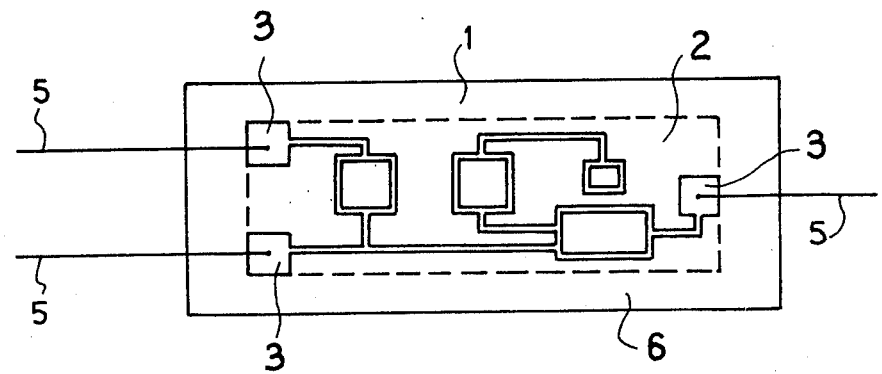
FIG. 1 is a plane view of a chip on which an integrated circuit has been fabricated.

In FIG. 1, there is shown a block or chip 1 having an integrated circuit represented schematically and bearing legend 2. It has three contact pads 3 on which have been soldered connecting wires 5. The dotted line indicates the lateral and longitudinal limits of the integrated circuit. The integrated circuit is typically of the type having field effect transistors.

According to the invention, the substrate which constitutes the chip 1 has been cut with a zone or border 6 around the circuit. It is of the minimum area required to separate the chips without spoiling the edges of the circuit 2. (During manufacture many integrated circuits are formed on a slice or wafer which is then cut into chips or blocks.)

Figure 2:
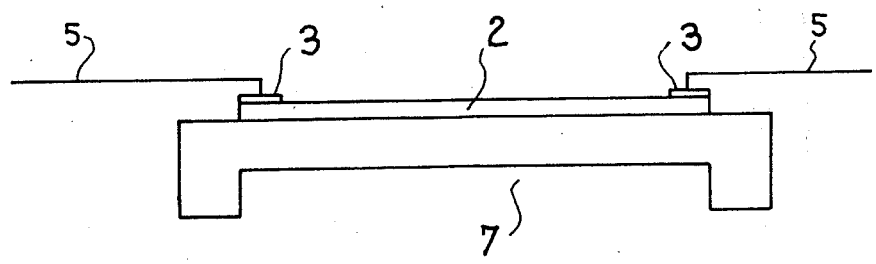
FIG. 2 is a longitudinal cross-section view of the chip of FIG. 1.

In FIG. 2, it can be seen that the substrate has been reduced in thickness, at 7 particularly on the opposite side from the integrated circuit. The thickness of the substrate is thus decreased from 150 microns to 30 microns. This operation can be effected by photoetching or other known techniques.

By these two steps, which reduce to a minimum the dimensions and the thickness of the chip, there is a decrease in the device's rigidity and consequently an increase in the extent of its deformation when a given force is applied, and an increase in its sensitivity, while a diminution of size facilitates its use within the body.

FIG. 3 represents a measuring device of the invention mounted by one of its ends in a catheter. Transducer 1 is mounted in a support 8 to provide a cantilever-type configuration. An opening 9 in the middle of the support 8 is connected to the central channel or lumen of the catheter and allows the air pressure in a measuring chamber 11 to be adjusted by connecting it to a source of reference pressure such as the atmosphere; this chamber 11, housing the transducer 1, being hermetically isolated from the medium (gas or fluid) whose pressure is to be measured. The wires 5 to the transducer run along grooves 12 and are soldered to connecting electrical conductors 13 mounted in the support. A hollow cylindrical guide member or mandrel 14 having a central aperture is inserted and imperviously secured at one of its ends to a mandrel support 15 which is integrally mounted within a protective cover 16 making up the casing of the distal tip of the catheter.

Across the other, free end of the mandrel 14, a thin resilient membrane 17 is stretched to imperviously seal the central aperture of mandrel 14 and to form, together with supports 8 and 15 and casing 16; the sealed measuring chamber 11. This membrane, made of natural rubber, is thin enough (about 17 hundredths of a millimeter) to allow the pressure external to the chamber 11 applied to it, to be accurately transmitted in spite of its displacement. The membrane 17 is secured to the free end of the mandrel 14 by a binding wire 18 made for example of plastic tied around an annular groove in the outer wall of mandrel 14. An aperture in protective cover 16 allows the membrane 17 to be brought substantially flush with the casing 16 and the external pressure to be exerted on membrane 17. This pressure is transmitted to the unattached tip of the transducer by means of a core or rod 19 which slides freely within the central opening of the mandrel 14. This core, which has a diameter of about 45 hundredths of a millimeter is held in place between the elasticity of transducer 1 and the elasticity of membrane 17. A tip 21, rounded at the end to prevent trauma at the time the instrument is introduced or manipulated in the body, completes the micro-probe.

The silicon chip which constitutes transducer 1 is about 1.8 millimeters long, 0.9 millimeters wide and its thickness varies from 40 to 200 microns except along the area constituting the circuit where it is reduced to about 30 microns.

Elastic membrane 17 which covers mandrel 14, ensures impermeability and allows pressure to be transmitted to transducer 1 by the displacements of the core 19. It is made of natural rubber instead of a synthetic material. It has been discovered that natural rubber is best used in this arrangement since it does not put an initial strain on the core, this strain being due to the fact that the elasticity of a sheet of synthetic material is not the same in all directions.

In addition, this membrane 17 is tied to mandrel 14 by a binding wire 18 and not by any form of adhesive. In this way, the tension along the circumference of the membrane is kept uniform. This results in an increase in the linearity of the displacement of the transducer in relation to the pressure exerted on the membrane.

Core 19 is held in place only by the elasticity of the transducer 1 and the membrane 17, and is not otherwise attached to either of these members in any way. This eliminates any strain in the displacements of core 19 due to the elasticity of an adhesive or other fixative. Since such strains vary with the temperature, the result is an instrument that is more precise because it is independent of the temperature.

With a difference in pressure of 300 mm of mercury between the inside and the outside of the membrane, the displacement of the membrane (and of the transducer) is on the order of a few microns. This makes it possible to obtain signals of an amplitude of 6 volts. These displacements are small and impart a high frequency response from the transducer, e.g. greater than 2,000 Hz. This enables at the same time a reading of both pressure and the intracardiac sounds (the latter of which has a working frequency band stopping at 1,000 Hz.)

FIG. 4 shows another embodiment of a device for measuring pressure. This one is situated outside the catheter. A protective cover 16 is shown with a mandrel support 15 attached. Transducer 1 is mounted in support 8 which is also fixed to cover 16. A mandrel 32, mounted in an opening in the support mandrel 15, is covered with a membrane 33 similar to the membranes described in the preceding devices. A core 34 moves in a compartment inside mandrel 32. This core is long enough to touch both transducer 1 and membrane 33 thus transmitting the pressure exerted on the membrane to transducer 1. As in the preceding embodiments, measuring chamber 11 is connected to the exterior (or to a pressurized enclosure) through an opening 9 in the center of the catheter.

FIG. 4 clearly shows a particular feature of this device which is that the core 34 (which transmits pressure to transducer 1) has a far greater diameter than the cores used in preceding devices. The diameter of this core is 2.7 millimeters instead of 0.45 millimeters. The device is therefore much more sensitive.

This instrument is designed principally to measure pressure inside an organ, as, for example, in the brain pan, without being itself introduced inside the brain.

In order to effect this operation, part of the device consisting of membrane 33 and the exterior surface of mandrel support 15 is applied to the organ. A measurement of pressure is possible only if the area of the device applied to the organ is a large, flat surface.

In the device described above, mandrel support 15 is much larger than protective cover 16 to which it is attached and the exterior surface of membrane 33 is situated along the same plane as the support face of support mandrel 15.

This tends to make the measurement of pressure less dependent on the force with which the device is applied against the organ whose pressure is being measured, and facilitates the orientation of the pickup against the membrane.

The embodiment shown in perspective in FIG. 5 is a catheter provided with two pressure gauges. In this case, and contrary to preceding embodiments, the transducer itself provides an air-tight barrier between the outside and the measuring chamber, and serves as the deformable membrane upon which pressure is exerted. These gauges have a chip 1 encased in a window cut into a flat surface 35.

According to a feature of the present invention, the chip constitutes an impermeable barrier between the measuring chamber and the outside because its edges are fixed to the edges of the window in a rigid manner. Thus the displacements of the chip are due only to the pressure exerted, without any sort of interference from the elasticity of an intermediary membrane. In addition, this method of attaching the chip reduces the risk of loss of seal.

Finally, the small dimensions of this transducer (1.8 millimeters long and 0.9 millimeters wide) allow it to be placed at the forward end of the catheter at 36 in a direction transverse to its axis. By using a transducer 50 microns thick, signals greater than 500 millivolts for a difference in pressure of 300 mm Hg have been obtained.

This arrangement permits pressure to be measured in two directions. It then becomes possible to correlate the average pressure obtained by the lateral transducer and the dynamic pressure obtained by the frontal transducer. An evaluation can then be made of the speed of flux of the fluid into which the catheter has been immersed.

Conducting rings can be added to the device. These rings 37 enable potentials to be picked up and electrocardiagrams to be recorded.

Most of the embodiments described herein suggest medical applications and particularly cardiac catheterizations, but it is obvious that the invention can be applied to probes with industrial uses. The device described in FIG. 4, which has greatly improved sensitivity, is especially well adapted to precisely measure external pressures.

I claim:

1. A device for measuring pressure of a medium comprising: a chip of semiconducting material whereon an integrated circuit including at least one field effect transistor sensitive to deformation is formed; means for defining a chamber housing said chip and impervious to said medium the pressure of which is to be measured relatively to that within said chamber, said chamber defining means including: a casing, a fixed support integrally secured to said casing and fixedly carrying one end of said chip, a mandrel-shaped hollow guide member having a central opening and one end tightly secured to said casing so as to locate one end of said central opening adjacent the other, free end of said chip, and a resilient membrane stretched across and secured to the other end of said hollow guide member for imperviously covering the other end of said central opening; and a rod-shaped core freely movably inserted inside said central opening having ends respectively in unattached contact with said membrane and said other, free end of said chip for transmitting the deformations of said membrane under pressure to said chip by axial displacements of said core.

2. Device as claimed in claim 1, wherein said resilient membrane is made of natural rubber and is stretched across said other end of said guide member by binding means.

3. Device as claimed in claim 1, wherein said fixed support includes an opening for connecting said chamber to a medium providing reference pressure.

4. Apparatus for measuring the pressure in a fluid, which comprises:
a housing having a chamber formed therein;
an integrated circuit transducer fastened at one end to said housing and extending upwardly into said chamber, said transducer including at least one field-effect transistor which is sensitive to deformation;
a mandrel-shaped guide member fastened to said housing, said guide member having a longitudinally extending bore therethrough and being positioned such that said bore is aligned with the other end of said transducer;
a resilient membrane stretched across and secured to said guide member to imperviously cover one end of said bore, said membrane being positioned proximate a window in the outer wall of said housing to thereby contact the fluid whose pressure is to be measured; and
a rod-shaped core slideably positioned inside said bore, the ends of said core respectively contacting said membrane and said other end of the transducer for transmitting deformations of said membrane under pressure to said transducer by the axial displacement of said core.

5. Apparatus according to claim 4 wherein said resilient membrane comprises natural rubber and is secured to said guide member by binding means.

6. Apparatus according to claim 4 wherein said housing further includes an opening into said chamber to connect said chamber to a source of a reference pressure.

* * * * *